United States Patent [19]

Sugitachi et al.

[11] 4,265,233

[45] May 5, 1981

[54] MATERIAL FOR WOUND HEALING

[75] Inventors: Akio Sugitachi, Koube; Kunihiko Takagi, Kyoto; Yasunori Yabushita, Yamatotakada, all of Japan

[73] Assignee: Unitika Ltd., Amagasaki, Japan

[21] Appl. No.: 27,637

[22] Filed: Apr. 6, 1979

[30] Foreign Application Priority Data

Apr. 12, 1978 [JP] Japan .................................. 53/43466
Oct. 24, 1978 [JP] Japan ................................ 53/131116

[51] Int. Cl.³ .............................................. A61F 13/00
[52] U.S. Cl. ................................................... 128/156
[58] Field of Search .............................. 128/155–156, 128/296, 260, 261, 269, 270, 271, 292, 325, 326, 335.5, DIG. 22, 334 R; 435/177–178, 182, 217

[56] References Cited

U.S. PATENT DOCUMENTS

| 2,465,357 | 3/1949 | Correll | 128/156 |
|---|---|---|---|
| 2,512,616 | 6/1950 | Eberl et al. | 128/156 |
| 2,533,004 | 12/1950 | Ferry et al. | 128/156 |
| 2,772,999 | 12/1956 | Masci et al. | 128/156 |
| 3,249,109 | 5/1966 | Maeth et al. | 128/156 |
| 3,419,006 | 12/1968 | King | 128/156 |

OTHER PUBLICATIONS

*Merck Index*, 9th Ed. p. 3873.
*Principles of Internal Medicine*, Harrison, 1958, pp. 300–303.

Primary Examiner—Robert W. Michell
Assistant Examiner—C. F. Rosenbaum
Attorney, Agent, or Firm—Sughure, Rothwell, Mion, Zinn and Macpeak

[57] ABSTRACT

A wound healing material having blood coagulation Factor XIII fixed thereto. This material promotes the formation of stabilized fibrin at a wound site and is effective for a long period of time, thereby protecting the wound and promoting its healing.

24 Claims, No Drawings

MATERIAL FOR WOUND HEALING

BACKGROUND OF THE INVENTION

1. Field of the Invention

This invention relates to a wound protecting and healing material.

2. Description of the Prior Art

A gelatin sponge having thrombin fixed thereto has been known as a healing material to be applied to a wound site such as a cut, scratch, etc., an incision from a surgical operation, and a cavity left from a tooth extraction (Japanese Pat. No. 41111/70). The thrombin contained in the gelatin acts on the fibrinogen at the wound to form a fibrin mass and thus stops the bleeding. The fibrin formed in this manner is a non-stabilized fibrin which is soluble in acids, urea, etc. and is susceptible to decomposition by plasmin. Thus, healing is frequently very slow.

Blood coagulation Factor XIII is a known blood coagulating factor having the ability to stabilize fibrin [see C. G. Curtis, L. Lorand, *Methods in Enzymology*, 45, 177, Academic Press (1976)]. This factor acts directly on non-stabilized fibrin and participates in the formation of isopeptide linkages among the fibrin molecules. Blood coagulation Factor XIII has been formulated into commercially available preparations, but there has been no instance in which it has been fixed to the substrate of a wound healing material.

SUMMARY OF THE INVENTION

It is an object of this invention to provide a wound healing material which promotes healing by the formation of stabilized fibrin.

Various investigations made to achieve the above object have led to the discovery that by fixing blood coagulation Factor XIII to a material, stabilized fibrin is formed which is effective for a long period of time.

According to this invention, there is provided a wound healing material capable of effectively promoting the formation of stabilized fibrin at a wound site which is effective for a long period of time. This material comprises a structure in such forms as a monofilament, a fibrous assembly, a film or a sponge having blood coagulation Factor XIII fixed thereto.

DETAILED DESCRIPTION OF THE INVENTION

The term "structure" as used herein with respect to the wound healing material of this invention refers to all conventional materials used in healing a wound site, which may have various forms such as monofilaments; fibrous assemblies, such as cotton, paper, non-woven fabrics, woven fabrics and knitted fabrics; films; sponges; etc. For example, surgical sutures (monofilaments, twisted yarns or knitting yarns), absorbent pads, bandages, burn dressings and packings for tooth cavities in the form of cotton, paper, non-woven fabrics, woven fabrics, knitted fabrics, films and sponges are within the meaning of the term "structure" as it is used in this specification. Furthermore, the term "structure" includes absorbable materials such as gelatin sponges as discussed in greater detail below.

Examples of the materials which make up such structures are shown below:

(A) Natural polymers

Cellulose, viscose rayon, cupraammonium rayon, cellulose acetate, carboxymethyl cellulose, methyl cellulose, agarose, dextran, pullulan, pectin, alginic acid, chitin, polysaccharides such as mucopolysaccharides, and proteins such as wool, silk, collagen, galatin and casein.

(B) Synthetic polymers

Polymers of olefins such as ethylene, propylene, 1-butene, 1-pentene and isobutylene, polymers of halogenated olefins such as vinyl chloride, vinylidene chloride, trifluoroethylene and tetrafluoroethylene, polymers of aromatic vinyl compounds such as styrene, divinyl benzene, α-methylstyrene or vinylpyridine, polymers of dienes such as butadiene or isoprene, polymers of N-vinyl compounds such as N-vinylamine or N-vinylpyrrolidone, polyvinyl alcohol and the esters thereof such as polyvinyl alcohol acetate, polymers of vinyl ethers such as vinyl methyl ether and tetramethylene glycol divinyl ether, polymers of sulfur-containing vinyl compounds such as vinyl sulfone or vinyl sulfoxide, polymers of unsaturated aldehydes such as acrolein, polymers of unsaturated ketones such as methyl vinyl ketone, polymers of $\alpha,\beta$-unsaturated carboxylic acids such as acrylic acid, methacrylic acid, maleic acid or fumaric acid, polymers of $\alpha,\beta$-unsaturated carboxylic acid esters such as methyl acrylate, ethyl acrylate, methyl methacrylate, ethyl methacrylate or maleic acid monomethyl ester, polymers of $\alpha,\beta$-unsaturated carboxylic acid chlorides such as acryloyl chloride or methacryloyl chloride, polymers of $\alpha,\beta$-unsaturated acid anhydride such as acrylic anhydride, methacrylic anhydride and maleic anhydride, polymers of $\alpha,\beta$-unsaturated nitriles such as acrylonitrile or methacrylonitrile, polymers of $\alpha,\beta$-unsaturated carboxylic acid amides such as acrylamide or methacrylamide, polyalkyleneimines such as polyethyleneimine, polyethers such as polyphenylene oxide, polymethylene oxide, polyethylene oxide or polytetramethylene oxide, polypeptides such as polyglutamic acid, polyalanine, polylysine, polyaspartic acid or polyphenylalanine, polyamides such as nylon-3, nylon-4, nylon-5, nylon-6, nylon-7, nylon-11, nylon-12, nylon-6,6, nylon-6,10, poly(m-phenyleneisophthalamide), or poly(p-phenylene terephthalamide), polyesters derived from polycarboxylic acids such as terephthalic acid, isophthalic acid, adipic acid, maleic acid, fumaric acid, or trimellitic acid and polyols such as ethylene glycol, propylene glycol, butylene glycol, pentaerythritol or bisphenol A, polyesters derived from hydroxycarboxylic acids such as glycolic acid, lactic acid or hydroxypivalic acid, silicone rubbers such as dimethylpolysiloxane, methylphenylpolysiloxane, methylvinylpolysiloxane, cyanoalkylmethylpolysiloxanes, and fluoroalkylmethylpolysiloxanes, polyurethanes derived from polyisocyanates such as toluene diisocyanate, xylene diisocyanate, phenylene diisocyanate, ethylene diisocyanate, diphenylmethane diisocyanate and toluene triisocyanate and polyols such as polyethylene glycol, polypropylene glycol or polyesters containing a hydroxy group at both terminals, formaldehyde resins such as phenol-formaldehyde resins, xylene-formaldehyde resins, urea-formaldehyde resins or melamine-formaldehyde resins, polymers containing a tetracyclic ring such as polyimides, polybenzimidazoles and polythiazoles, polycarbonates derived from bisphenol A and phosgene, polysulfones derived from bisphenol A and 4,4'-dichlorodiphenylsulfone.

Linear copolymers, crosslinked copolymers, graft copolymers and blocked copolymers containing units of the monomeric components of the above-exemplified polymers can also be used as materials for producing the structure of the wound healing material of this invention.

A suitable weight average molecular weight for these polymers so that the polymers have the mechanical strength required of a wound healing material is about 7,000 to 1,000,000, preferably about 10,000 to 500,000.

Among the aforesaid materials, cellulose, cellulose derivatives such as viscose rayon, cupraammonium rayon and cellulose acetate, such proteins as collagen and gelatin, polyvinyl alcohol and its derivatives, such polypeptides as polyglutamic acid, polyalanine, polylysine and polyaspartic acid, such polyamides as nylon-6 and nylon-6,6, and such polyesters as polyethylene terephthalate, polybutylene terephthalate and polyglycolic acid and polylactic acid, and polyurethane are preferred.

The present invention is characterized by the fact that blood coagulation Factor XIII (hereafter "Factor XIII") is fixed to the above structures. Preferably, thrombin is fixed together with Factor XIII because it further promotes the formation of non-stabilized fibrin at a wound site.

Factor XIII used in this invention is a fibrin stabilizing factor which acts directly on non-stabilized fibrin and forms isopeptide linkages among the fibrin molecules. Factor XIII is obtained from the blood or placenta of man and cattle and is commercially available. For application to a wound site of a human, the use of Factor XIII derived from humans is preferred.

The thrombin used in this invention is a protease capable of converting fibrinogen into fibrin. Thrombin is separated from the blood of man, cattle, swine, etc., but for application to man, the use of human thrombin is preferred. Thrombin is also available.

Factor XIII and thrombin can be fixed to a structure in such a form as a monofilament, fibrous assembly, film or sponge by covalent bonding, ionic bonding adsorption, or entrapping using conventional techniques such as those described in O. Zaborsky, *Immobilized Enzymes*, CRC Press, 1973.

When the aforesaid structure constituting the wound healing material contains a reactive functional group capable of forming a covalent bond (e.g., a carboxyl group, a chlorotriazinyl group, an azido group, a diazonium group, an epoxy group, a formyl group, an acid anhydride group, a bromoacetyl group, an isocyanate group or an iminocarbonate group, or an ion exchange group such as an amino group, an ammonium ion, a carboxyl group, a carboxylate group, a sulfoxyl group or a sulfonate group) Factor XIII and thrombin (hereafter this discussion will refer to the use of Factor XIII and thrombin together, however, it is to be understood that the use of Factor XIII without thrombin constitutes one embodiment of this invention) may be covalently or ionically bonded to the structure by treating it with a solution of Factor XIII and thrombin. When the structure contains little or no functional group capable of forming a covalent bond or an ionic exchange group, Factor XIII and thrombin can be bonded to the structure after introducing such a group into the structure by known polymer reactions.

Some examples of bonding Factor XIII and thrombin to various structures are described below.

Proteins such as silk, collagen, casein or gelatin contain an amino group and a carboxyl group which are functional groups capable of forming a covalent bond and at the same time, ion exchange groups. Structures made of these proteins can have Factor XIII and thrombin covalently or ionically bonded thereto without prior treatment. In the case of covalent bonding, it is preferred to use a dehydro-condensation agent such as dicyclohexyl carbodiimide and 1-cyclohexyl-3-(2-morpholinoethyl)-carbodiimide-metho-p-toluenesulfonate to form a peptide bond with the amino group and the carboxyl group in the protein. In this case the dehydro-condensation agent is dissolved in an amount of about 0.1 to 20% by weight, preferably about 1 to 10% by weight, in water or a mixture of water with a water-miscible solvent such as methyl alcohol, ethyl alcohol, propyl alcohol, dioxane, tetrahydrofuran, dimethylformamide or dimethylsulfoxide. A structure composed of the above protein is treated with a mixed solution of the dehydro-condensation agent solution and the Factor XIII and thrombin solution, or first with the dehydro-condensation agent solution and subsequently with the Factor XIII and thrombin solution or vice versa, at a temperature of about −20° to about 60° C., preferably 0° to 40° C., for about 10 minutes to about 72 hours, preferably for 30 minutes to 24 hours.

Alternatively, it is possible to first react the proteinaceous structure with a polyaldehyde such as dialdehyde starch, glutaraldehyde or glyoxal, or a polycarboxylic acid anhydride such as maleic anhydride/methyl vinyl ether copolymer, maleic anhydride/styrene copolymer or maleic anhydride/ethylene copolymer to introduce a formyl or acid anhydride group, and then fix (bond) Factor XIII and thrombin covalently.

The reaction between the proteinaceous structure and the polyaldehyde is carried out by dissolving the polyaldehyde in a concentration of about 0.1 to 50% by weight, preferably about 0.5 to 30% by weight, and treating the proteinaceous structure with the resulting polyaldehyde solution. The suitable treating temperature is about −20° C. to 70° C., preferably about 0° to 50° C., and the reaction time is generally about 5 minutes to 24 hours, preferably about 20 minutes to 8 hours.

The reaction between the proteinaceous structure and the polycarboxylic acid adhydride is carried out by dissolving the polycarboxylic acid anhydride in acetone, tetrahydrofuran, benzene, toluene, dimethylformamide, dimethylsulfoxide, or a mixture of any of these in a concentration of about 0.1 to 30% by weight, preferably about 0.5 to 10% by weight, and treating the proteinaceous structure with the resulting solution. A suitable treating temperature is about −20° C. to 60° C., preferably about 0° to 40° C., and the treating time is generally about 5 min. to 24 hrs., preferably about 20 min. to 6 hrs.

A structure made of a hydroxy group-containing polymeric material such as cotton, viscose rayon, cuprammonium rayon, cellulose, and cellulose derivatives such as cellulose acetate, or polyvinyl alcohol is first treated with a polyaldehyde such as glutaraldehyde, glyoxal or dialdehyde starch to introduce a formyl group into the structure. Then the structure containing the formyl group is treated with Factor XIII and thrombin thereby to bond Factor XIII and thrombin covalently. The reaction between the structure composed of the hydroxyl group-containing polymeric material and the polyaldehyde is carried out by dissolving the polyaldehyde in an acidic aqueous solution containing hydrochloric acid, sulfuric acid, acetic acid or the like in a concentration of about 0.1 to 50% by weight, preferably about 0.5 to 20% by weight, and treating the structure with the resulting solution at a temperature of about −20° C. to 60° C., preferably about 0° to 40° C., for about 5 minutes to about 24 hours, preferably 10 minutes to 10 hours.

Alternatively, an iminocarbonate group can be introduced into the structure by using bromocyan; a bromoacetyl group can be introduced by using bromoacetyl bromide; an acid anhydride group can be introduced by using a polycarboxylic anhydride such as maleic anhydride/methyl vinyl ether copolymer, maleic anhydride/styrene copolymer or maleic anhydride/ethylene copolymer; an isocyanate group can be introduced by using a polyisocyanate; and a chlorotriazinyl group can be introduced by using cyanuric chloride; and Factor XIII and thrombin are fixed to the modified structure.

Reaction of the structure made of a hydroxyl group-containing polymeric material with bromocyan can be performed in accordance with the method of R. Axen, J. Porath and S. Ernback, *Nature*, 214, 1302 (1967). Reaction of the structure made of the hydroxyl group-containing polymeric material with bromoacetyl bromide can be performed by referring to the method of Israeli Pat. No. 18207 (1965).

Reaction of the structure made of the hydroxyl group-containing polymeric material with polymaleic anhydride is carried out by dissolving the polymaleic anhydride in acetone, tetrahydrofuran, benzene, toluene, dimethylformamide, dimethylsulfoxide, or a mixture of any of these in a concentration of about 0.1 to 30% by weight, preferably about 0.5 to 10% by weight, optionally adding a catalyst such as hydrochloric acid, sulfuric acid or acetic acid to the resulting solution in a concentration of about 0.01 to 10% by weight, preferably about 0.05 to 2% by weight, and treating the structure with the solution at about 0° to 100° C., preferably about 20° to 80° C., for about 10 min. to 24 hrs., preferably about 30 min. to 10 hrs.

Reaction of the structure made of the hydroxyl group-containing polymeric material with the polyisocyanate is carried out by dissolving the polyisocyanate in dimethylformamide, methyl ethyl ketone, tetrahydrofuran or a mixture of any of these in a concentration of about 0.1 to 50% by weight, preferably about 0.5 to 20% by weight, optionally adding a catalyst such as N-methyl morpholine or triethylene diamine in a concentration of about 0.001 to 10% by weight, preferably about 0.01 to 1% by weight, and treating the structure with the solution at about 20° to 120° C., preferably about 40° to 90° C., for about 5 min. to 24 hrs., preferably about 20 min. to 10 hrs.

Reaction of the structure made of the hydroxyl group-containing polymeric material with cyanuric chloride can be performed by referring to G. Kay, E. M. Crook, *Nature*, 216, 514 (1964), and A. K. Sharp, G. Kay, M. D. Lilly, *Biotechnology and Bioengineering*, 11, 363 (1970).

An epoxy group can be introduced into the structure made of the hydroxyl group-containing polymeric material by reacting the structure with an unsaturated acid chloride such as crotonic anhydride, tetrahydrophthalic anhydride or 10-undecenoyl chloride, and epoxidizing the product with chloroperbenzoic acid or hydrogen peroxide.

The structure having introduced thereinto a reactive functional group such as a formyl group, an iminocarbonate group, a bromoacetyl group, an acid anhydride group, an isocyanate group, a chlorotriazinyl group or an epoxy group is aminated by treatment with a polyamine such as polyethyleneimine, and carboxylated by treatment with an aminocarboxylic acid such as glycine or epsilon-aminocaproic acid. The treatment with the polyamine or aminocarboxylic acid is carried out by reacting the structure having a reactive functional group with an aqueous solution of the polyamine or the aminocarboxylic acid in a concentration of about 0.1 to 30% by weight, preferably about 0.5 to 10% by weight, at a temperature of about 0° to 100° C., preferably about 10° to 60° C., for a period of about 10 min. to 48 hrs., preferably about 30 min. to 24 hrs. The structure having thus introduced thereinto an amino group or carboxyl group, an ion exchange group is capable of ionically bonding Factor XIII and thrombin thereto.

In the case of a structure made of a carboxyl-terminated polymeric material such as a polyamide or polyester, an acid anhydride group can be introduced into the structure by treating the structure with a polyamine such as polyethyleneimine in the presence of a dehydrocondensation agent such as dicyclohexyl carbodiimide, and subsequently, treating the resulting product with a polycarboxylic acid anhydride such as a maleic anhydride/methyl vinyl ether copolymer, in accordance with the method of Japanese patent application (OPI) No. 10378/77. By treating the structure having an acid anhydride group introduced thereinto with Factor XIII and thrombin, the Factor XIII and thrombin can be covalently bonded thereto. By reacting the structure having an acid anhydride group introduced thereinto with water at about 10° to 100° C., preferably about 20° to 60° C., for a period of about 10 min. to 48 hrs., preferably about 1 to 24 hrs., a carboxyl group (which is an ion exchange group) is formed. In this manner, Factor XIII and/or thrombin can be ionically bonded to the carboxyl group-containing structure.

When a structure made of a carboxyl-terminated polymeric material such as a polyamide or polyester is treated first with benzidine or hydrazine and then with nitrous acid by the method of W. E. Hornby, H. Filippusson, *Boochimica et Biophysica Acta*, 220, 343 (1970), a diazonium group or an azido group can be introduced into the structure. By treating the structure having introduced thereinto the diazonium or azido group with Factor XIII and thrombin, the Factor XIII and thrombin can be covalently bonded.

In introducing a reactive functional group or an ion exchange group into the structure in the above-described manner, it is necessary to select a solvent which does not dissolve the structure. Fixation of Factor XIII to the structure having a functional group or an ion exchange group to thereby convalently or ionically bond the Factor XIII and thrombin to the structure is performed by treating the structure with a solution of the Factor XIII. Fixation of Factor XIII and thrombin is carried out by treating the structure with a solution containing the Factor XIII and thrombin, or by first treating it with a solution of Factor XIII and subsequently with a solution of thrombin, or in the reverse order. Factor XIII and thrombin dissolve in water or a mixture of water with a water-miscible solvent such as methanol, ethanol, propanol, acetone, tetrahydrofuran, dioxane, dimethylsulfoxide or dimethylformamide in a concentration of about 1 to about 2,000 units/ml, preferably about 5 to 500 units/ml. One unit of Factor XIII corresponds to the Factor XIII activity of 1 ml of fresh standard human plasma. One unit of thrombin corresponds to the unit defined by the U.S. National Institute of Health (see *Minimum Requirement for Dried Thrombin*, 2nd Revision, Division of Biologic Standards, National Institute of Health, Bethesda, Maryland, 1946). A suitable temperature for the treatment of Factor XIII and thrombin is about −20° to 70° C., preferably about 0° to 40° C., and the suitable treating time is about 1 min. to 48 hrs., preferably about 2 min. to 24 hrs. In fixing Factor XIII and thrombin, the pH of the solution should be adjusted to about 3 to about 10, preferably 4 to 9. For this purpose, a buffer such as a phosphate buffer or an acetate, an acid such as hydrochloric acid, or an alkali such as sodium hydroxide is used. As required, a protein (not more than 10 g/liter) such as albumin or gelatin, or a salt (not more than 2 moles/liter) such as sodium chloride is added as a stabilizer.

In producing the wound healing material of this invention, Factor XIII and thrombin can be fixed to the structure in the form of a monofilament, a fibrous assembly, a film, a sponge or the like by adsorption in the following manner. Factor XIII and thrombin are dissolved in a solvent capable of wetting the structure, and the structure is treated with the resulting solution at a temperature of about −20° to 60° C., preferably about 0° to 40° C., for a period of about 10 min. to 48 hrs., preferably about 30 min. to 24 hrs., thereby effecting adsorption of Factor XIII and thrombin to the structure. Suitable solvents are water and mixtures of water and water-miscible solvents such as methanol, ethanol, propanol, acetone, tetrahydrofuran, dioxane, dimethylsulfoxide and dimethylformamide. Suitable concentration of Factor XIII and thrombin are about 1 to 2,000 units/ml, preferably about 5 to 500 units/ml.

The wound healing material of this invention can also be produced by fixing Factor XIII and thrombin by entrapping. Entrapping comprises entrapping Factor XIII and thrombin in the fine lattices of a gel or in a polymeric film. Suitable materials used in this method are absorbable materials such as collagen, gelatin, polyglycolic acid, polylactic acid, a glycolic acid/lactic acid copolymer, polyglutamic acid and amylose. Entrapping of Factor XIII and thrombin in the gel lattices is effected by dissolving, emulsifying or suspending Factor XIII and thrombin and an absorbable material such as collagen or gelatin, and processing the resulting solution, emulsion or suspension into a structure having the shape of a film, a sponge, a filament or a non-woven fabric by a conventional wet or dry method. As required, the absorbable polymer may be crosslinked by adding a curing agent such as glyoxal, glutaraldehyde or trimethylol melamine or by application of ultraviolet or ionizing radiation to increase the mechanical strength of the polymer and adjust the absorbability of the polymer.

Examples of the solvent that can be used to dissolve, emulsify or suspend the absorbable polymer and Factor XIII and thrombin are water, methanol, ethanol, propanol, acetone, tetrahydrofuran, dioxane, dimethylformamide, dimethylsulfoxide, methylene chloride, and mixtures of these. Suitable concentrations of Factor XIII and thrombin are about 1 to 2,000 units/ml, preferably about 5 to 500 units/ml. A suitable concentration of the absorbable polymer is about 0.1 to 50% by weight, preferably about 0.5 to 30% by weight.

For molding the resulting solution by a dry method, Japanese Patent Publication No. 41111/70 may be referred to. The method of Japanese Patent Publication No. 41111/70 comprises adding a foaming agent such as myristyl sodium sulfate to a solution containing a gelatin, after sterilizing the solution foaming, adding the glyoxal as a denaturant in an amount of 0.003 to 0.007 g per 1 g of gelatin at the time of foaming to mold and strengthen the gelatin, and lyophilizing the product in the mold. For molding of the solution by a wet method see *Methods in Enzymology*, Vol. 44, p. 169, edited by K. Mosbach, Academic Press, 1976.

The amount of Factor XIII and thrombin fixed to the above structure varies over a wide range in accordance with a type of wound, the time for which the wound healing material is used and the form of the wound healing material. Generally, the amount of Factor XIII and thrombin fixed thereto is 1 to 100,000 units per gram of the wound healing material, preferably 5 to 20,000 units per gram.

In the production of the wound heating material of this invention, a calcium ion which participates in the activation of Factor XIII can be fixed to the structure together with the Factor XIII and thrombin. The calcium ion is generally added to the structure as calcium chloride in an amount of 0.1 $\mu$mol to 1 m mole, preferably 0.5 $\mu$mol to 200 $\mu$mol. As required, pharmaceuticals such as antiplasmins, antibiotics, anti-virals, sulfonamides and anti-infectives can be fixed to the structure together with Factor XIII and thrombin in the production of the wound healing material of this invention. Antiplasmin is an inhibitor of plasmin which is a fibrin-dissolving enzyme, and therefore, it inhibits fibrinolytic activity by obstructing plasmin. Accordingly, a wound healing material having anti-plasmin fixed thereto together with Factor XIII and thrombin can promote the formation of fibrin by inhibiting fibrinolytic activity. Examples of the antiplasmin are aprotinin extracted from the lungs of cattle, natural substances such as pepstatin, leupeptin, antipain or chymostatin separated from the culture broths of microorganisms, epsilon-aminocaproic acid, tranexamic acid, and gabexate mesilate. Epsilon-aminocaproic acid and tranexamic acid are especially preferred. Examples of antibiotics are penicillin, tetracycline, chlorotetracycline, bacitracin, streptomycin, neomycin, polymyxin, gramicidin, oxytetracycline, chloramphenicol, erythromycin and the like. Examples of anti-virals are idoxuridine and the like. Examples of sulfanamide are sulfacetamide, sulfamethazole, sulfamethazine, sulfisoxazole and the like. Examples of anti-infectives are nitrofurazone, sodium propionate and the like. Since the amount of the pharmaceutical fixed to the above structure together with Factor XIII and thrombin varies in a wide range in accordance with a kind of pharmaceutical, the desired healing effects and the time of which the wound healing material is used, it is not practical to determine the range of the amount of the pharmaceutical. However, generally, the amount of the pharmaceutical fixed thereto is 1 microgram to 100 milligram per 1 g of the wound healing material, preferably 10 microgram to 10 milligram.

The wound healing material of this invention can be used to protect a wound site, for example, an injury caused by cutting, scratching, etc., a burn, ulcers generated on the surface of the body, wound surfaces in surgical operation, cavities left after tooth extraction, etc. Since it can effectively promote the formation of stabilized fibrin at the wound site for long periods of time, it strikingly expedites healing, and simultaneously has an effect of alleviating localized pains. A wound healing material having both Factor XIII and thrombin fixed thereto has a far greater heal promoting effect than that having only Factor XIII fixed thereto because thrombin promotes the formation of non-stabilized fibrin which is a precursor of stabilized fibrin.

When an absorbable material such as collagen, gelatin, polyglycolic acid, polylactic acid, a glycolic acid/lactic acid copolymer, polyglutamic acid, or amylose is used as a material for the wound healing material of this invention, the structure need not be removed after healing has been achieved. It is used especially preferably at sites which require the promotion of formation of stabilized fibrin in the body such as anastomotic sites. Among these, gelatin, collagen, polyglycolic acid and polylactic acid are especially suitable.

The wound healing material of this invention can be easily sterilized by using a gaseous germicide such as ethylene oxide. It can also be sterilized by irradiation of X-rays, gamma-rays, neutrons, and electrons.

The following Examples illustrate the present invention more specifically, however, these Examples are not to be construed as limiting. Factor XIII Konzentrat (a product of Berhringewerke AG, derived from placenta) was used as the Factor XIII. Human plasma thrombin (a product of Midori Juji K.K.) was used as the thrombin.

Formation of stabilized fibrin was confirmed in the following manner. In the case of a structure having only Factor XIII fixed thereto, the structure was treated with an aqueous solution containing thrombin (25 units/ml) and $Ca^{+2}$ (0.025 mole/liter) to activate the Factor XIII, and a non-stabilized fibrin film was formed on the surface of the structure using fibrinogen and thrombin. The sample was allowed to stand at 37° C. for 1 hour, and the formation of stabilized fibrin was tested for. In the case of a structure having both Factor XIII and thrombin fixed thereto, the structure was treated with an aqueous solution containing $Ca^{++}$ to activate Factor XIII, put into a 0.5% aqueous solution of fibrinogen, and allowed to stand for 1 hour at 37° C. Then, it was tested to determine whether the fibrin formed on the surface of the structure was stabilized fibrin. Non-stabilized fibrin dissolved in 1% monochloroacetic acid, but stabilized fibrin did not. Hence, the solubility of the fibrin film formed in the above manner in 1% monochloroacetic acid was tested to determine the formation of stabilized fibrin.

Example 1

In accordance with the method of G. Kay et al. [G. Kay, E. M. Crook, Nature, 216, 514 (1967)], a surgical gauze (cotton made, 5 cm×5 cm) was dipped in 20 ml of a 1 N aqueous solution of sodium hydroxide. With stirring, an acetone solution of cyanuric chloride (formed by dissolving 3.69 g of cyanuric chloride in 20 ml of acetone) was added. The reaction was performed at 20° C. for 10 minutes. The gauze having a chlorotriazinyl group introduced thereinto was washed with acetone and then with water, and treated with an aqueous solution of Factor XIII (63 units/ml) at 20° C. for 3 minutes, followed by washing with physiological saline.

The fibrin film formed on the surface of the surgical gauze having Factor XIII covalently bonded thereto did not dissolve in 1% monochloroacetic acid.

EXAMPLE 2

A surgical gauze was treated in the same manner as in Example 1 except that a mixture composed of 4 ml of a solution of Factor XIII (125 units/ml) and 4 ml of physiological saline solution of thrombin (200 units/ml) was used instead of the solution of Factor XIII.

The fibrin formed on the surface of the surgical gauze having Factor XIII and thrombin covalently bonded thereto did not dissolve in 1% monochloroacetic acid.

EXAMPLE 3

A polyethylene terephthalate taffeta (10 cm×10 cm) was dipped in a mixture of a 10% aqueous solution of polyethyleneimine and methanol in 5 times the amount by volume of the polyethyleneimine solution, and allowed to stand at room temperature for 30 minutes. Then a 4% by weight methanol solution of dicyclohexyl carbodiimide was added in an amount twice the volume of the aqueous polyethyleneimine solution, and the taffeta was further allowed to stand at room temperature for 2 hours. The taffeta was withdrawn, washed with methanol, and dried. The taffeta treated with polyethyleneimine was placed in an acetone solution containing 3% by weight of a methylvinylether/maleic anhydride copolymer, allowed to stand at room temperature for 2 hours, and then washed with acetone. The resulting taffeta was dried, allowed to stand at 4° C. for 24 hours in a solution of Factor XIII (63 units/ml), and washed with physiological saline.

The fibrin film formed on the surface of the taffeta having Factor XIII covalently bonded thereto did not dissolve in 1% monochloroacetic acid.

EXAMPLE 4

A polyethylene terephthalate taffeta was treated in the same manner as in Example 3 except that a mixture consisting of 4 ml of a solution of Factor XIII (125 units/ml) and 4 ml of physiological saline (200 units/ml) was used instead of the solution of Factor XIII.

The fibrin formed on the surface of the taffeta having both Factor XIII and thrombin covalently bonded thereto did not dissolve in 1% monochloroacetic acid.

EXAMPLE 5

A gelatin sponge (5 cm×2.5 cm×0.5 cm) (a product of Yamanouchi Pharmaceutical Co., Ltd.) was dipped in 10 ml of an aqueous solution of Factor XIII (63 units) for 10 minutes, and then lyophilized for 20 hours. The fibrin formed on the surface of the gelatin sponge having Factor XIII ionically bonded thereto did not dissolve in 1% monochloroacetic acid.

EXAMPLE 6

The same gelatin sponge as used in Example 5 was dipped in 10 ml of the mixed solution of Factor XIII and thrombin used in Example 2, and then lyophilized for 20 hours. The fibrin formed on the surface of the gelatin sponge having both Factor XIII and thrombin ionically bonded thereto did not dissolve in 1% monochloroacetic acid.

EXAMPLE 7

A commercially available absorbable suture of collagen (Cut Gut, Plain Type, NESCO Suture Laboratories), a commercially available absorbable braided suture of polyglycolic acid (a product of American Cyanamid Company) and an absorbable braided suture of polylactic acid prepared in accordance with Japanese Patent Publication No. 31696/70 were each treated in the same way as in Example 5. As a result, the fibrin formed on any of the surfaces of any of the sutures having Factor XIII fixed thereto did not dissolve in 1% monochloroacetic acid.

Factor XIII was fixed by ionic bonding in the case of the absorbable collagen suture, and by adsorption, in the case of the polyglycolic acid and polylactic acid sutures.

EXAMPLE 8

The three absorbable sutures used in Example 7 were treated in the same manner as in Example 6. The fibrin formed on the surface of any of the sutures having both Factor XIII and thrombin fixed thereto did not dissolve in 1% monochloroacetic acid.

Factor XIII and thrombin were fixed to the absorbable collagen suture by ionic bonding, and to the polyglycolic acid and polylactic acid sutures by adsorption.

EXAMPLE 9

The same commercially available absorbable suture of collagen as used in Example 7 was dipped in a mixture consisting of 2 ml of an aqueous solution of Factor XIII (125 units/ml), 2 ml of physiological saline solution of thrombin (200 units/ml) and 4 ml of an aqueous solution of 1-cyclohexyl-3-(2-morpholinoethyl)carbodiimide-metho-p-toluenesulfonate (40 mg/ml), allowed to stand for 20 hours at 70° C., and then washed with physiological saline.

The fibrin formed on the surface of the absorbable suture of collagen having both Factor XIII and thrombin covalently bonded thereto did not dissolve in 1% monochloroacetic acid.

EXAMPLE 10

A test tube was charged with 8 ml of distilled water, 2 g of gelatin and 50 mg of sodium lauryl sulfate, and the mixture was dissolved by warming it to 30° to 35° C. The solution was vigorously stirred while it was kept at 30° to 35° C., to form it to 5 times its original volume. At the time of foaming, 0.04 ml of a 40% aqueous solution of glyoxal and 1 ml of an aqueous solution of Factor XIII (63 units/m) were added. The resulting foam was cast into a sheet form, and lyophilized. The fibrin formed on the surface of the gelatin sponge did not dissolve in 1% monochloroacetic acid.

Factor XIII was fixed to the gelatin sponge by entrapping and ionic bonding.

EXAMPLE 11

A gelatin sponge was prepared in the same manner as in Example 1 except that the mixed solution of Factor XIII and thrombin used in Example 2 was used instead of the aqueous solution of Factor XIII. The fibrin formed on the surface of the gelatin sponge did not dissolve in 1% monochloroacetic acid.

Factor XIII and thrombin were fixed to the gelatin sponge by entrapping and ionic bonding.

While the invention has been described in detail and with reference to specific embodiments thereof, it will be apparent to one skilled in the art that various changes and modifications can be made therein without departing from the spirit and scope thereof.

What is claimed is:

1. A wound healing material capable of effectively promoting the formation of stabilized fibrin at a wound site over a long period of time, said material comprising a structure having a substance fixed thereto, said substance consisting essentially of blood coagulation Factor XIII.

2. The healing material of claim 1, wherein the structure is an absorbable material.

3. The healing material of claim 2, wherein the absorbable material is gelatin.

4. The healing material of claim 2, wherein the absorbable material is collagen.

5. The healing material of claim 2, wherein the absorbable material is polyglycolic acid.

6. The healing material of claim 2, wherein the absorbable material is polylactic acid.

7. The healing material of claim 1, wherein said Factor XIII is fixed in an amount sufficient to promote the formation of stabilized fibrin.

8. A wound healing material capable of effectively promoting the formation of stabilized fibrin at a wound site over a long period of time, said material comprising a structure having a substance fixed thereto, said substance consisting essentially of blood coagulation Factor XIII and thrombin.

9. The healing material of claim 8, wherein the structure is an absorbable material.

10. The healing material of claim 9, wherein the absorbable material is gelatin.

11. The healing material of claim 9, wherein the absorbable material is collagen.

12. The healing material of claim 9, wherein the absorbable material is polyglycolic acid.

13. The healing material of claim 9, wherein the absorbable material is polylactic acid.

14. The healing material of claim 8, wherein said Factor XIII and thrombin are fixed in amounts sufficient to promote the formation of stabilized fibrin.

15. The healing material of claims 1 or 8, wherein calcium ion is additionally fixed to the structure.

16. The healing material of claims 1 or 8, wherein a pharmaceutical is additionally fixed to the structure.

17. The healing material of claim 16, wherein said pharmaceutical is selected from the group consisting of antiplasmins, antibiotics, antivirals, sulfanamides and anti-infectives.

18. The healing material of claim 1 or 8, wherein said structure is in the form of a mono-filament, a fibrous assembly, a film, or a sponge.

19. The healing material of claim 1 or 8, wherein said healing material is a surgical suture.

20. The healing material of claim 1 or 8, wherein said healing material is a dressing.

21. The healing material of claim 1 or 8, wherein said healing material is a bandage.

22. The healing material of claim 1 or 8, wherein said healing material is a sponge.

23. The healing material of claim 1 or 8, wherein said healing material is a filling for a tooth extracted cavity.

24. The healing material of claim 2 or 9, wherein said healing material is a gelatin sponge.

* * * * *